United States Patent [19]

Helsley et al.

[11] Patent Number: 5,045,539
[45] Date of Patent: Sep. 3, 1991

[54] (1H-INDOLO(3,2-C)QUINOLINE-DERIVATIVES, COMPOSITIONS CONTAINING SAME, USEFUL FOR TREATING PAIN, PSYCHOSIS OR CONVULSIONS

[75] Inventors: Grover C. Helsley, Pluckemin; John J. Tegeler, Bridgewater, both of N.J.; Kirk D. Shoger, Minneapolis, Minn.

[73] Assignee: Hoechst-Roussel Pharmaceuticals Inc., Somerville, N.J.

[21] Appl. No.: 654,113

[22] Filed: Feb. 6, 1991

Related U.S. Application Data

[62] Division of Ser. No. 377,341, Jul. 10, 1989, Pat. No. 5,006,531.

[51] Int. Cl.$^5$ .................. C07D 471/20; C07D 487/20; A61K 31/44; A61K 31/55
[52] U.S. Cl. .................................. 514/212; 514/278; 540/543; 546/15
[58] Field of Search ............... 514/212, 278; 540/543; 546/15

[56] References Cited

U.S. PATENT DOCUMENTS 4,874,767 10/1989 Munro et al. .................. 514/278

*Primary Examiner*—Alan L. Rotman
*Attorney, Agent, or Firm*—Tatsuya Ikeda

[57] ABSTRACT

There are disclosed compounds having the formula

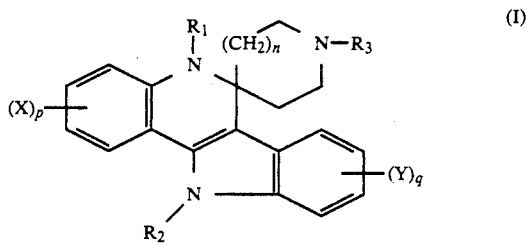

where
n is 0, 1, or 2;
p and q are each independently 1, 2 or 3;
each X and each Y are independently hydrogen, loweralkyl, loweralkoxy, halogen, hydroxy, nitro, amino, loweralkylamino, diloweralkylamino, trifluoromethyl or loweralkylthio;
$R_1$ and $R_2$ are each independently hydrogen or loweralkyl; and
$R_3$ is hydrogen, loweralkyl, loweralkylcarbonyl, arylloweralkyl or aminocarbonyl;
which are useful as analgesic, antipsychotic and anticonvulsant agents.

13 Claims, No Drawings

(1H-INDOLO(3,2-C)QUINOLINE-DERIVATIVES, COMPOSITIONS CONTAINING SAME, USEFUL FOR TREATING PAIN, PSYCHOSIS OR CONVULSIONS

This is a division of a prior application Ser. No. 377,341, filed July 10, 1989, now U.S. Pat. No. 5,006,531.

The present invention relates to compounds of the formula,

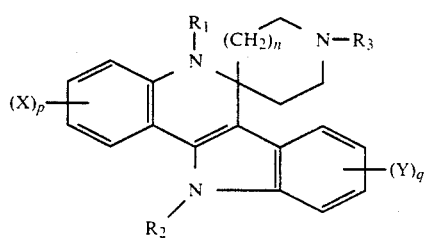

where
n is 0, 1, or 2;
p and q are each independently 1, 2 or 3;
each X and each Y are independently hydrogen, loweralkyl, loweralkoxy, halogen, hydroxy, nitro, amino, loweralkylamino, diloweralkylamino, trifluoromethyl or loweralkylthio;
$R_1$ and $R_2$ are each independently hydrogen or loweralkyl; and
$R_3$ is hydrogen, loweralkyl, loweralkylcarbonyl, aryl-loweralkyl or aminocarbonyl;
which are useful as analgesic, antipsychotic and anticonvulsant agents.

Throughout the specification and the appended claims, a given chemical formula or name shall encompass all stereo, geometrical and optical isomers thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-butyl, pentyl and hexyl.

Unless otherwise stated or indicated, the term cycloalkyl denotes an alicyclic hydrocarbon group containing 3 to 7 carbon atoms. Examples of said cycloalkyl include cyclopropyl, cyclohexyl and cyclohetyl.

Unless otherwise stated or indicated, the term halogen shall mean fluorine, chlorine, bromine or iodine.

Unless otherwise stated or indicated, the term aryl shall mean an unsubstituted phenyl group or a phenyl group substituted with 1, 2 or 3 substituents each of which being independently loweralkyl, loweralkoxy, halogen, hydroxy or trifluoromethyl.

The compounds of this invention are prepared by utilizing one or more of the steps described below.

Throughout the description of the synthetic steps, the definitions of n, p, q, X, Y, $R_1$, $R_2$ and $R_3$ are as given above unless otherwise stated or indicated.

STEP A

A compound of Formula II is allowed to react with acetonitrile in the presence of $BCl_3$ and $AlCl_3$ in a suitable medium such as anhydrous benzene or the like and thereafter the resultant product is hydrolyzed to afford a compound of Formula III. Typically, this reaction is conducted by reacting compound II with $BCl_3$ in anhydrous benzene under a refluxing condition, cooling the solution, adding acetonitrile and $AlCl_3$ to the solution, refluxing the mixture and thereafter carefully quenching the reaction. See, for instance, Sugasawa, *J. Amer. Chem. Soc.*, Volume 100(15), 4842 (1978).

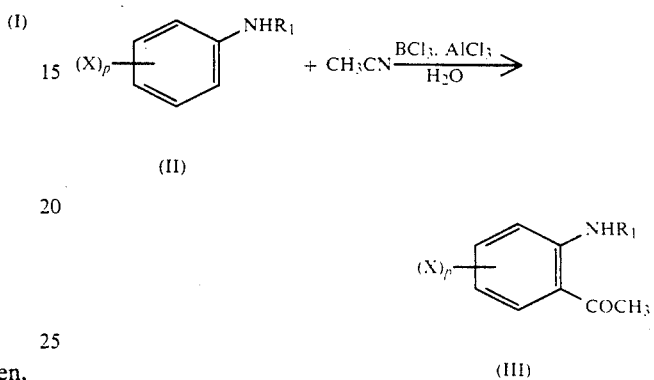

STEP B

Compound III is allowed to react with a phenylhydrazine of Formula IV in a routine manner known to the art to afford a compound of Formula V. Typically, this reaction is conducted in a suitable medium such as a mixture of glacial acetic acid and ethanol under a refluxing condition. See also the article by Sugasawa cited above.

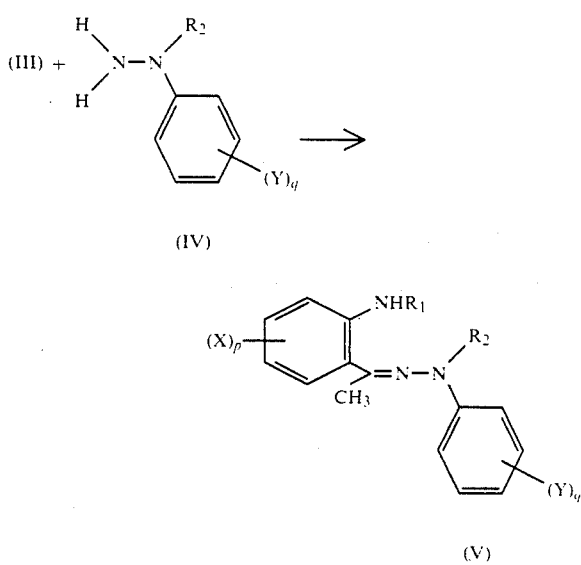

STEP C

Fisher indole synthesis is conducted with compound V in a routine manner known to the art to afford a compound for Formula VI. Typically, this reaction is conducted in the presence of polyphosphoric acid at a temperature of about 80° to 140° C.

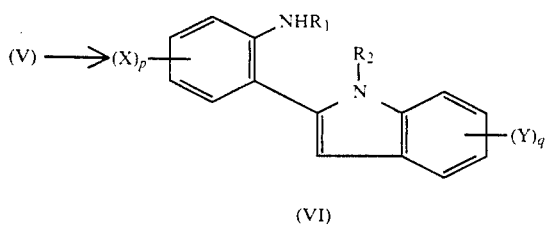

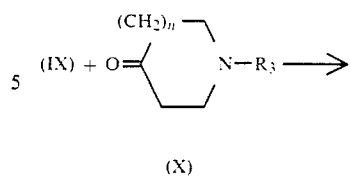

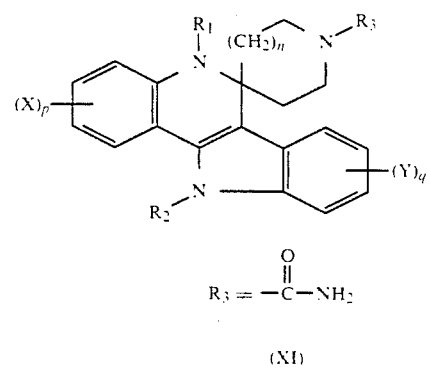

STEP D

As a special case, where a compound of Formula VI in which $R_1$ is methyl is desired, one can use the following reaction route as an alternative to the reaction steps described above.

Thus, a compound of Formula VII obtained from STEP C above is allowed to react with formic acid and dicyclohexylcarbodiimide in a routine manner known to the art to afford a compound of Formula VIII and thereafter compound VIII is reduced with LiAlH$_4$ in a routine manner known to the art to afford a compound of Formula IX.

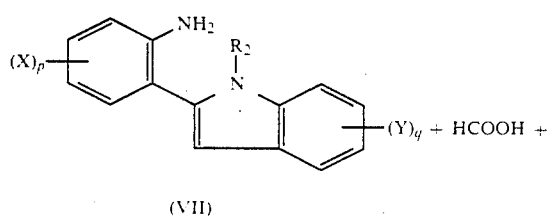

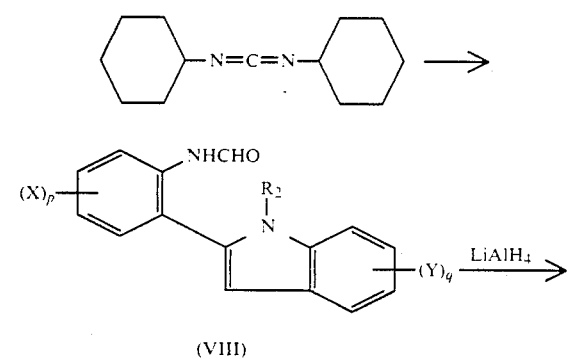

STEP E

Compound IX is allowed to react with a ketone of Formula X (where $R_3$ is not aminocarbonyl) to afford a compound of Formula XI. Typically, this reaction is conducted in a suitable solvent such as a mixture of glacial acetic acid and ethanol at a temperature of 50° to 80° C.

STEP F

As a special case, where a compound of Formula XI in which $R_3$ is ethyl is desired, one can use the following reaction route as an alternative to STEP E described above.

Thus, a compound of Formula XIa obtained in STEP E is reduced with LiAlH$_4$ in a suitable medium such as tetrahydrofuran at a temperature of about 0° to 65° C. to afford a compound of Formula XIb.

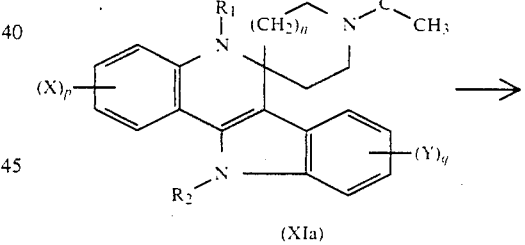

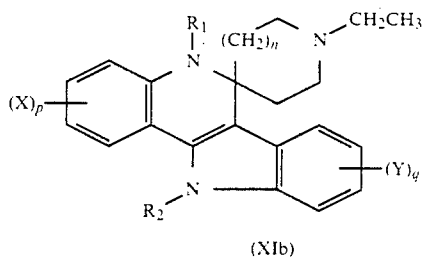

STEP G

A compound of Formula XIc obtained from STEP E is allowed to react with (CH$_3$)$_3$SiNCO in the presence of K$_2$CO$_3$ to afford a compound of Formula XId. Typically, this reaction is conducted in a suitable solvent such as tetrahydrofuran at a temperature of 0° to 65° C.

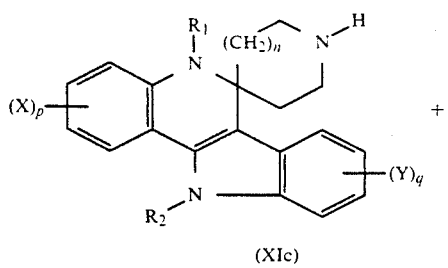

(XIc)

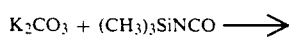

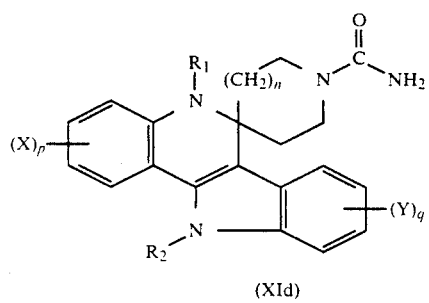

(XId)

Compounds I of the present invention are useful as analgesic agents due to their ability to alleviate pain in mammals. The activity of the compounds is demonstrated in the 2-phenyl-1,4-benzoquinone-induced writhing (PQW) test in mice, a standard assay for analgesics [Proc. Soc. Exptl. Biol. Med., 95,729 (1957)]. Results of this test for some of the compounds of this invention are presented in Table 1.

TABLE 1

| ANALGESIC ACTIVITY | |
|---|---|
| Compound | PQW |
| 1',5-diemthyl-5,6-dihydrospiro-[1H-indolo[3,2-c]quinoline-6,4'-piperidine]fumarate, hemiethanolate | $ED_{50}$ = 10.3 mg/kg. s.c. |
| 1'-phenethyl-5,6-dihydrospiro-1H-indolo[3,2-c]quinoline-6,4'-piperidine]fumarate | −55% at 5 mg/kg. s.c. |
| 1'-acetyl-5,6-dihydrospiro-1H-indolo[3,2-c]quinoline-6,4'-piperidine] (Reference Compound) | −66% at 20 mg/kg. s.c. |
| Pentazocine | −50% at 1.3 mg/kg, s.c. |

The compounds of the present invention having formula I are useful as antipsychotic agents.

Antipsychotic activity is determined in the climbing mice assay by methods similar to those described by P. Protais, et al., Psychopharmacol., 50, 1 (1976) and B. Costall, Eur. J. Pharmacol., 50, 39, (1978).

The subject CK-1 male mice (23-27 grams) are group-housed under standard laboratory conditions. The mice are individually placed in wire mesh stick cages (4"×4" by 10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

Climbing Behavior

| Mice With: | Score |
|---|---|
| 4 paws on bottom (no climbing) | 0 |
| 2 paws on the wall (rearing) | 1 |
| 4 paws on the wall (full climb) | 2 |

Mice consistently climbing before the injection of apomorphine are discarded.

With full-developed apomorphine climbing, the animals are hanging onto the cage walls, rather motionless, over long periods of time. By constrat, climbs due to mere motor stimulation usually last only a few seconds.

The climbing scores are individually totaled (maximum score: 6 per mouse over 3 readings) and the total score of the control group (vehicle intraperitoneally; apomorphine subcutaneously) is set to 100%. $ED_{50}$ values with 95% confidence limits, calculated by a linear regression analysis, of some of the compounds of this invention are presented in Table 2.

Results of the climbing mice assáy for some of the compounds of this invention along with a result for a reference compounds are presented in Table 2.

TABLE 2

| ANTIPSYCHOTIC ACTIVITY | |
|---|---|
| Compound | Climbing Mice Assay |
| 1',5-diemthyl-5,6-dihydrospiro-[1H-indolo[3,2-c]quinoline-6,4'-piperidine]fumarate, hemiethanolate | $ED_{50}$ = 19.8 mg/kg. i.p. |
| 3-chloro-5,1'-dimethyl-5,6-dihydrospiro[1H-indolo-[3,2-c]quinoline-6,4'-piperidine]dihydrochloride (Reference Compounds) | $ED_{50}$ = 13.2 mg/kg. i.p. |
| Clozapine | $ED_{50}$ = 8.1 mg/kg. s.c. |
| Sulpiride | $ED_{50}$ = 14.5 mg/kg. s.c. |

Antipsychotic response is achieved when the compounds of this invention are administered to a subject requiring such treatment as an effective oral, parenteral or intraveneous dose of from 0.01 to 50 mg/kg of body weight per day. It is be understood, however, that for any particular subject, specific dosage regimens should be adjusted according to the individual need and the professional judgement of the person administering or supervising the administration of the aforesaid compound. It is to be further understood that the dosages set forth herein are exemplary only and they do not to any extent, limit the scope of practice of the invention Compounds I of the present invention are also useful as anticonvulsant agents due to their anticonvulsant activity in mammals. Anticonvulsant activity is measured in the mouse using the supramaximal electroshock (SES) assay described in Arch. Int. Pharmacodyn. 92: 97-107, 1952. In this procedure groups of male mice, 18-30 grams, are used. Drugs are prepared using distilled water and, if insoluble, a surfactant is added. Control animals receive vehicle. Drugs are routinely administered intraperitoneally (i.p.). The dosage volume is 10 ml/kg. A primary screen is given a 30 minute pretreat.. The animal's eyes are placed across the output terminals of an A.C. shocker that delivers 206 volts rms for 300 msec. Electrode paste coats the animal's eyes at the point of contact with the terminals. A compound is considered to give protection if the mouse does not exhibit extensor tonus. Protection is expressed as normalized percent inhibition relative to vehicle control.

A time response is carried out using six animals/group. Animals are tested at 30, 60 and 120 minutes postdrug. Additional time periods are tested if indicated by previous tests. When the peak activity time has been determined, a dose response is initiated using 10 animals/group at that time period. The $ED_{50}$ and 95% confidence interval are calculated by computer probit analysis.

Test results of supramaximal electroshock for a compound of this invention along with a result for a reference compound are presented in Table 3.

TABLE 3

ANTICONVULSANT ACTIVITY

| Compound | |
|---|---|
| 1'-ethyl-5,6-dihydrospiro-[1H-indolo[3,2-c]quinoline-6,4'-piperidine] (Reference Compound) | −80% at 60 mg/kg, i.p. |
| Chlordiazepoxide | $ED_{50}$ = 8.0 mg/kg, i.p. |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

Examples of the compounds of this invention include:
5,6-dihydrospiro[1H-indolo[3,2-c]quinoline-6,4'-piperidine];
1'-methyl-5,6-dihydrospiro[1H-indolo[3,2-c]quinoline-6,4'-piperidine];
1',5-dimethyl-5,6-dihydrospiro[1H-indolo[3,2-c]quinoline-6,4'-piperidine];
3-chloro-5,1'-dimethyl-5,6-dihydrospiro[1H-indolo[3,2-c]quinoline-6,4'-piperidine];
1'-acetyl-5,6-dihydrospiro[1H-indolo[3,2-c]quinoline-6,4'-piperidine];
1'-ethyl-5,6-dihydrospiro[1H-indolo[3,2-c]quinoline-6,4'-piperidine];
1'-propyl-5,6-dihydrospiro[1H-indolo[3,2-c]quinoline-6,4'-piperidine];
1'-aminocarbonyl-5,6-dihydrospiro[1H-indolo[3,2-c]quinoline-6,4'-piperidine];
1'-phenylmethyl-5,6-dihydrospiro[1H-indolo[3,2-c]quinoline-6,4'-piperidine];
1'-phenethyl-5,6-dihydrospiro[1H-indolo[3,2-c]quinoline-6,4'-piperidine];
1',5,11-trimethyl-5,6-dihydrospiro[1H -c]quinoline-6,4'-piperidine];
1'11-dimethyl-5,6-dihydrospiro[1H-indolo[3,2-c]quinoline-6,4'-piperidine];
5,11-dimethyl-5,6-dihydrospiro[1H-indolo[3,2-c]quinoline-6,4'-piperidine];
1',5-dimethyl-3-trifluoromethyl-5,6-dihydrospiro[1H-indolo[3,2-c]quinoline-6,4'-piperidine];
3-chloro-1',5,11-trimethyl-5,6-dihydrospiro[1H-indolo[3,2-c]quinoline-6,4'-piperidine];
8-bromo-1',5-dimethyl-5,6-dihydrospiro[1H-indolo[3,2-c]quinoline-6,4'-piperidine];
1',5-dimethyl-2-methoxy-5,6-dihydrospiro[1H-indolo[3,2-c]quinoline-6,4'-piperidine];
1'-cyclopropylmethyl-5-methyl-5,6-dihydrospiro[1H-indolo[3,2-c]quinoline-6,4'-piperidine];
2-fluoro-1',5-dimethyl-5,6-dihydrospiro[1H-indolo[3,2-c]quinoline-6,4'-piperidine];
3-fluoro-1',5-dimethyl-5,6-dihydrospiro[1H-indolo[3,2-c]quinoline-6,4'-piperidine];
8-methylthio-1',5-dimethyl-5,6-dihydrospiro[1H-indolo[3,2-c]quinoline-6,4'-piperidine];
3-bromo-1',5-dimethyl-5,6-dihydrospiro[1H-indolo[3,2-c]quinoline-6,4'-piperidine];

3-methylthio-1',5-dimethyl-5,6-dihydrospiro[1H-indolo[3,2-c]quinoline-6,4'-piperidine];

The following examples are presented in order to illustrate this invention.

EXAMPLE 1

4-Chloro-2-(methylamino)acetophenone phenylhydrazone

A solution of 95 g of 3-chloro-N-methylaniline in 100 ml of benzene was added dropwise to ice-cold 1.0M $BCl_3$/benzene (804 ml) under $N_2$ and the solution was refluxed for 2 hours. The solution was cooled to room temperature and 70 ml of anhydrous $CH_3CN$ was added followed by 98 g of $AlCl_3$ in several portions. This mixture was refluxed for 20 hours. The reaction was quenched, with ice bath cooling, by careful addition of 200 ml of water followed by one liter of 3.4M HCl. The mixture was refluxed for one hour, cooled and separated. The aqueous layer was extracted with $CH_2Cl_2$(2x). The combined organic extract was washed with brine and dried ($MgSO_4$). Concentration gave 30.8 g of brown oil. Proton NMR indicated ca 70:30 mixture of the desired 4-chloro-2-(methylamino)acetophenone and byproduct 2-chloro-6-(methylamino)acetophenone. This mixture was used directly below.

A mixture prepared from 28.5 g of the above acetophenones, 15.3 ml of phenylhydrazine, 9.0 ml of HOAc and 50 ml of EtOH was refluxed for 45 minutes. The solid, which crystallized on cooling to room temperature, was collected and washed with hexane to give 18.5 g of orange crystalline solid, m.p. 113°–116°. Recrystallization of 2.0 g of this solid from methanol gave 1.2 g of yellow needles, m.p. 118°–120° C.

ANALYSIS:

Calculated for $C_{15}H_{16}ClN_3$: 65.81% C; 5.89% H; 15.35% N.

Found: 65.73% C; 5.86% H; 15.34% N.

EXAMPLE 2

N-[2-(1H-Indol-2-yl)phenyl]formamide

To a solution prepared from 20 g of 2-(2-aminophenyl)indole, 12.7 ml of formic acid and 500 ml of THF was added 26 g of dicyclohexyl carbodiimide at room temperature under $N_2$. The resultant solution was stirred overnight at room temperature. The mixture was then filtered and the filtrate washed with aqueous $NaHCO_3$ (2x), $H_2O$ and saturated NaCl solution and dried ($MgSO_4$). Concentration gave a red oil which was purified by HPLC, using 1% $EtOAc/CH_2Cl_2$ as an eluent, to afford 11.45 g of solid, m.p. 147°–149° C.

ANALYSIS:

Calculated for $C_{15}H_{12}N_2O$: 76.25% C; 5.12% H; 11.86% N.

Found: 76.26% C; 5.10% H; 11.62% N.

EXAMPLE 3

5,6-Dihydrospiro[1H-indolo[3,2-c]quinoline-6,4'-piperidine]

To a mixture prepared from 8 g of 2-(2-aminophenyl)indole, 2.5 ml of acetic acid and 100 ml of ethanol was added 6.5 g of 4-poperidone•$H_2O$•HCl. The mixture was refluxed for 6 hours and thereafter cooled to room temperature. The resultant mixture was treated with dilute $NH_4OH$ and the resultant solid was collected, washed with water and dried. The crude product (9.15 g) was flash chromatographed using $CH_3OH$ as an eluent, and thereafter converted to the HCl salt. This salt was converted back to the free base using $CH_2Cl_2$/dilute $NH_4OH$ to give 5.96 g of solid, m.p. 257°–259° dec.

ANALYSIS:

Calculated for $C_{19}H_{19}N_3$: 78.86% C; 6.62% H; 14.52% N.

Found: 78.26% C; 6.73% H; 14.47% N.

EXAMPLE 4

1'-Methyl-5,6-dihydrospiro[1H-indolo[3,2-c]quinoline-6,4'-piperidine]

To a solution prepared from 8 g of 2-(2-aminophenyl)indole, 2.5 ml of acetic acid and 100 ml of ethanol was added 5.15 g of 1-methyl-4-piperidone. The mixture was refluxed for 6 hours. Concentration gave a gum which was triturated with dilute $NH_4OH$ and the resultant solid was collected. Flash chromatography using 10% $CH_3OH/CH_2Cl_2$ as an eluent gave 4.15 g of yellow solid, m.p. 228°–230° dec.

ANALYSIS:

Calculated for $C_{20}H_{21}N_3$: 79.17% C; 6.98% H; 13.85% N.

Found: 78.85% C; 7.09% H; 13.68% N.

EXAMPLE 5

1',5-Dimethyl-5,6-dihydrospiro[1H-indolo[3,2-c]quinoline-6,4'-piperidine]fumarate, hemiethanolate To a cooled solution of 1M $LiAlH_4$/THF (82.6 ml) was added a solution of 9.75 g of N-[2-(1H-indol-2-yl)phenyl]formamide in 150 ml of THF. After 30 minutes of stirring the solution was quenched with an $NH_4Cl$ solution, filtered and concentrated to give a brown oil. Flash chromatography using 10% $CH_2Cl_2$/hexane gave 7.18 g of blue oil.

To a solution of this oil in 70 ml of ethanol were added 2 ml of acetic acid and 4.3 ml of 1-methyl-4-piperidone. The mixture was refluxed for 6 hours. Concentration gave a mixture which was treated with a dilute $NH_4OH$ solution and the solid was collected. Flash chromatography using 5% $CH_3OH/CH_2Cl_2$ gave 3.5 g of green solid. The solid was converted to the fumate salt and recrystallized in ethanol to give 3.01 g of yellow solid, m.p. 257°–259° C. dec.

ANALYSIS:

Calculated for $C_{21}H_{23}N_3 \cdot C_4H_4O_4 \cdot 0.5C_2H_6O$: 68.40% C; 6.63% H; 9.20% N.

Found: 68.80% C; 6.64% H; 9.45% N.

EXAMPLE 6

3-Chloro-5,1'-dimethyl-5,6-dihydrospiro[1H-indolo[3,2-c]quinoline-6,4'-piperidine]dihydrochloride 4-Chloro-2-(methylamino)acetophenone phenylhydrazone (13 g) was added portionwise over 10 minutes to 130 g of polyphosphoric acid at 80° under $N_2$, during which the temperature was maintained below 100°. The resultant mixture was warmed at 100° for 1 hour and thereafter poured directly into excess water with stirring. The precipitated product was collected, washed with water and dried ($P_2O_5$) under high vacuum to give 12 g of tan solid which was a phosphate salt of 2-(4-chloro-2-methylaminophenyl)-1H-indole.

A mixture prepared from 5.5 g of this indole, 2.2 g of 1-methyl-4-piperidone, 10 ml of $BF_3 \cdot Et_2O$ and 30 ml of acetic acid was warmed at 70° under $N_2$ for 1 hour. The mixture was cooled and poured onto excess ice, made basic with 50% NaOH solution and extracted with $CH_2Cl_2$(2x). The extract was washed with a half saturated NaCl solution and dried (MgSO$_4$). Concentration gave 2.1 g of solid. This was converted to its dihydrochloride salt in EtOH/Et$_2$O to give 1.35 g of tan solid, m.p. 252°–255°.

ANALYSIS:

Calculated for C$_{21}$H$_{22}$ClN$_3$•sHCl: 59.38% C; 5.69% H; 9.89% N.

Found: 59.26% C; 5.60% H; 9.91% N.

EXAMPLE 7

1'-Acetyl-5,6-dihydrospiro[1H-indolo[3,2-c]quinoline-6,4'-piperidine]

To a solution prepared from 5 g of 2-(2-aminophenyl)indole, 100 ml of ethanol and 2 ml of glacial acetic acid was added dropwise 3 ml of 1-acetyl-4-piperidone. The resultant solution was refluxed for 6 hours and thereafter cooled, whereupon a solid precipitated. Filtration and washing with ether and hexane gave 3.95 g of yellow solid, m.p. 285°–287° dec.

ANALYSIS:

Calculated for C$_{21}$H$_{21}$N$_3$O: 76.10% C; 6.39% H; 12.68% N.

Found: 76.25% C; 6.36% H; 12.67% N.

EXAMPLE 8

1'-Ethyl-5,6-dihydrospiro[1H-indolo[3,2-c]quinoline-6,4'-piperidine]

A solution of 7.5 g of 1'-acetyl-5,6-dihydrospiro-[1H-indolo-[3,2-c]quinoline-6,4'-piperidine]in 60 ml of THF was added dropwise to 45 ml of 1M LiAlH$_4$/THF. The solution was stirred at room temperature for 30 minutes and thereafter quenched with NH$_4$Cl, filtered through celite and concentrated to give 9.2 g of crude product. Flash chromatography using 7% CH$_3$OH/CH$_2$Cl$_2$ as an eluent gave 3.5 g of solid, m.p. 238°–240° dec.

ANALYSIS:

Calculated for C$_{21}$H$_{23}$N$_3$: 79.46% C; 7.30% H; 13.24% N.

Found: 79.06% C; 7.37% H; 13.12% N.

EXAMPLE 9

1'-Propyl-5,6-dihydrospiro[1H-indolo[3,2-c]quinoline-6,4'-piperidine]maleate, monoethanolate To a mixture prepared from 7.8 g of 2-(2-aminophenyl)indole, 100 ml of ethanol and 2.5 ml of acetic acid was added 5.7 ml of 1-propyl-4-piperidone. The mixture was heated at reflux for 6 hours. The solution was cooled, concentrated and treated with a dilute NH$_4$OH solution. The resultant solid was collected, washed with water and dried to give 11.8 g of tan solid. This was flash chromatographed using 5% CH$_3$OH/CH$_2$Cl$_2$ as an eluent to give 2.8 g of light tan solid. The maleate salt was prepared in ethanol and recrystallized from ethanol to give 2.2 g of solid, m.p. 150°–153° dec.

ANALYSIS:

Calculated for C$_{22}$H$_{25}$N$_3$•C$_4$H$_4$O$_4$•C$_2$H$_6$O: 68.13% C; 7.15% H; 8.51% N.

Found: 68.00% C; 7.06% H; 8.49% N.

EXAMPLE 10

1'-Aminocarbonyl-5,6-dihydrospiro[1H-indolo-[3,2-c]quinoline-6,4'-piperidine]

To a solution of 4 g of 5,6-dihydrospiro[1H-indolo[3,2-c]quinoline-6,4'-piperidine] in 100 ml of THF were added 9.7 g of K$_2$CO$_3$ and 13.9 ml of trimethylsilyl isocyanate (32% xylene by weight). The mixture was stirred overnight at room temperature and filtered. Subsequently, an additional 5.6 ml of trimethylsilyl isocyanate was added and the resultant solution was stirred for 30 minutes at room temperature. Concentration gave a solid/gum mixture which was triturated with H$_2$O to give 3.07 g of solid, m.p. 265°–267° dec.

ANALYSIS:

Calculated for C$_{20}$H$_{20}$N$_4$O: 72.26% C; 6.07% H; 16.86% N.

Found: 71.70% C; 6.07% H; 16.61% N.

EXAMPLE 11

1'-Phenylmethyl-5,6-dihydrospiro[1H-indolo[3,2-c]quinoline-6,4'-piperidine]

To a mixture prepared from 7.6 g of 2-(2-aminophenyl)indole, 2.5 ml of acetic acid and 90 ml of ethanol was added 7.4 ml of 1-phenylmethyl-4-piperidone. The resultant solution was refluxed for 6 hours. Concentration gave a solid/gum mixture which was taken up in EtOH and treated with dilute NH$_4$OH. Filtration gave 12.45 g of yellow solid. This was recrystallized from CH$_3$OH/H$_2$O to give 9.0 g of yellow solid. High vacuum drying (90°) gave 2.6 g of dark yellow solid, m.p. 155°–157° C.

ANALYSIS:

Calculated for C$_{26}$H$_{25}$N$_3$: 82.29% C; 6.64% H; 11.07% N.

Found: 82.16% C; 6.68% H; 10.84% N.

EXAMPLE 12

1'-Phenethyl-5,6-dihydrospiro[1H-indolo[3,2-c]quinoline-6,4'-piperidine]fumarate Under N$_2$, 5 g of 2-(2-aminophenyl)indole was combined with 100 ml of EtOH, 2 ml of acetic acid and 4.9 g of 1-phenethyl-4-piperidone. The mixture was stirred at reflux for 2 hours. Concentration gave a gum which was triturated with a dilute ammonia solution to give a solid. HPLC using 7% EtOAc/CH$_2$Cl$_2$ as an eluent gave a solid which as converted to the fumarate salt in ethanol to give 2.8 g of solid, m.p. 216°–220° dec.

ANALYSIS:

Calculated for C$_{27}$H$_{27}$N$_3$•C$_4$H$_4$O$_4$: 73.06% C; 6.13% H; 8.45% N.

Found: 73.33% C; 5.86% H; 8.67% N.

We claim:

1. A compound of the formula

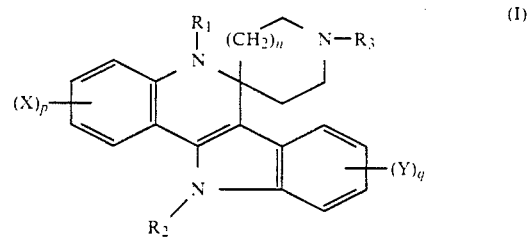

where n is 0 or 2;

p and are each independently 1, 2 or 3;

each X and each Y, are independently hydrogen, loweralkyl, loweralkoxy, halogen, hydroxy, nitro, amino, loweralkylamino, diloweralkylamino, trifluoromethyl or loweralkylthio;

R$_1$ and R$_2$ are each independently hydrogen or loweralkyl; and $R_3$ is hydrogen, loweralkyl, loweralkylcarbonyl, aryl-loweralkyl or aminocarbonyl;

or a pharmaceutically acceptable acid addition salt thereof.

2. The compound as defined in claim 1, wherein $R_1$ is hydrogen.

3. The compound as defined in claim 1, wherein $R_1$ is methyl.

4. The compound as defined in claim 1, wherein $R_2$ is hydrogen.

5. The compound as defined in claim 1, wherein each Y is hydrogen or halogen.

6. The compound as defined in claim 1, wherein each X is hydrogen or halogen.

7. The compound as defined in claim 1, wherein $R_1$ is hydrogen or methyl and $R_2$ is hydrogen.

8. The compound as defined in claim 7, wherein each Y is hydrogen or halogen.

9. The compound as defined in claim 7, wherein each X is hydrogen or halogen.

10. A pharmaceutical composition comprising a compound as defined in claim 1 in an amount effective for alleviating pain, psychosis or convulsion, and a suitable carrier therefor.

11. A method of treating a patient in need of relief from pain which comprises administering to the patient an effective pain alleviating amount of a compound as defined in claim 1.

12. A method of treating a patient in need of relief from psychosis which comprises administering to the patient an effective psychosis alleviating amount of a compound as defined in claim 1.

13. A method of treating a patient in need of relief from convulsion which comprises administering to the patient an effective convulsion alleviating amount of a compound as defined in claim 1.

* * * * *

UNITED STATES PATENT AND TRADEMARK OFFICE
CERTIFICATE OF CORRECTION

PATENT NO. : 5,045,539

DATED : September 3, 1991

INVENTOR(S) : G. C. Helsley et al

It is certified that error appears in the above-identified patent and that said Letters Patent is hereby corrected as shown below:

Column 12, line 62:
In Claim 1, line 5; insert --q-- after "p and ".

Signed and Sealed this

Seventeenth Day of November, 1992

Attest:

DOUGLAS B. COMER

Attesting Officer    Acting Commissioner of Patents and Trademarks